United States Patent
Retsina et al.

(10) Patent No.: US 9,315,750 B2
(45) Date of Patent: Apr. 19, 2016

(54) PROCESSES FOR PRODUCING BIOMASS PELLETS AND SUGARS

(71) Applicant: API Intellectual Property Holdings, LLC, Atlanta, GA (US)

(72) Inventors: Theodora Retsina, Atlanta, GA (US); Vesa Pylkkanen, Atlanta, GA (US)

(73) Assignee: API Intellectual Property Holdings, LLC, Atlanta, GA (US)

( * ) Notice: Subject to any disclaimer, the term of this patent is extended or adjusted under 35 U.S.C. 154(b) by 0 days.

(21) Appl. No.: 14/314,787

(22) Filed: Jun. 25, 2014

(65) Prior Publication Data

US 2015/0004654 A1    Jan. 1, 2015

Related U.S. Application Data

(60) Provisional application No. 61/839,912, filed on Jun. 27, 2013.

(51) Int. Cl.
| | |
|---|---|
| C12P 19/02 | (2006.01) |
| C12P 19/14 | (2006.01) |
| C13K 13/00 | (2006.01) |
| C10L 5/14 | (2006.01) |
| C10L 5/10 | (2006.01) |
| C10L 5/44 | (2006.01) |
| C13K 1/02 | (2006.01) |
| C10L 5/36 | (2006.01) |

(52) U.S. Cl.
CPC . *C10L 5/44* (2013.01); *C10L 5/143* (2013.01); *C10L 5/363* (2013.01); *C10L 5/445* (2013.01); *C12P 19/02* (2013.01); *C12P 19/14* (2013.01); *C13K 1/02* (2013.01); *C13K 13/00* (2013.01); *C13K 13/002* (2013.01)

(58) Field of Classification Search
None
See application file for complete search history.

(56) References Cited

U.S. PATENT DOCUMENTS

| | | | |
|---|---|---|---|
| 2009/0305374 A1* | 12/2009 | Retsina et al. | 435/165 |
| 2011/0056126 A1* | 3/2011 | Harvey et al. | 44/606 |
| 2012/0110896 A1* | 5/2012 | Coronella et al. | 44/307 |

* cited by examiner

*Primary Examiner* — Robert Yamasaki
*Assistant Examiner* — Charles Zoltan Constantine
(74) *Attorney, Agent, or Firm* — Ryan P. O'Connor

(57) ABSTRACT

In this disclosure, a process for producing biomass pellets and sugars from cellulosic biomass is provided, comprising: extracting the feedstock with steam and/or hot water and optionally with an acid catalyst, to produce cellulose-rich solids and an extract liquor containing hemicellulosic oligomers and lignin; separating the cellulose-rich solids from the extract liquor; filtering the extract liquor to remove at least some of the lignin, thereby generating a filter permeate comprising cleaned extract liquor containing the hemicellulosic oligomers and a filter retentate comprising a lignin-rich stream; hydrolyzing the hemicellulosic oligomers in the cleaned extract liquor with an acid or enzymes, to generate hemicellulosic monomers which are recovered; and pelletizing the cellulose-rich solids to form biomass pellets, wherein the pelletizing utilizes at least some of the lignin-rich stream as a binder or binder component.

18 Claims, 1 Drawing Sheet

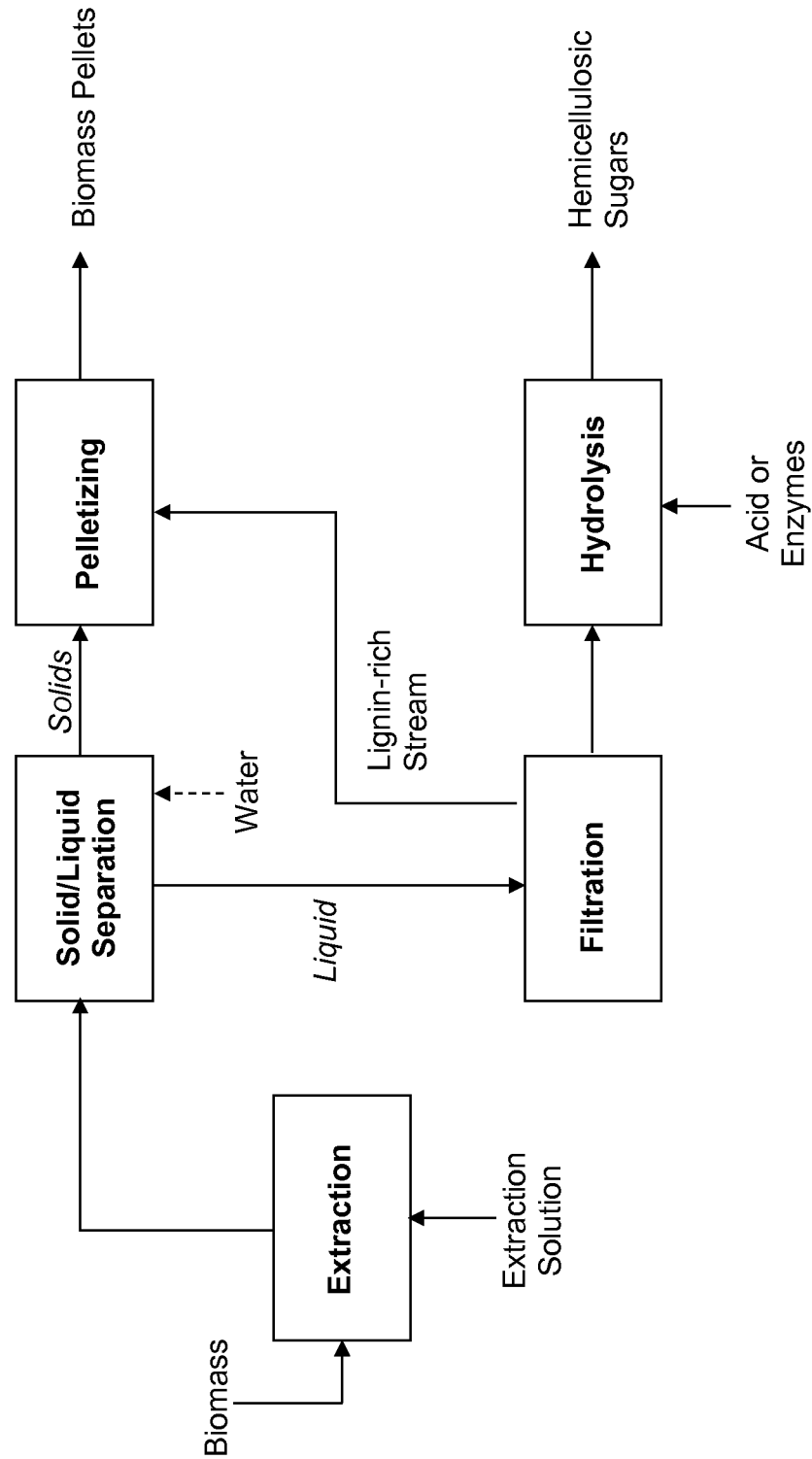

PROCESSES FOR PRODUCING BIOMASS PELLETS AND SUGARS

PRIORITY DATA

This patent application is a non-provisional patent application with priority to U.S. Provisional Patent App. No. 61/839,912, filed Jun. 27, 2013, which is hereby incorporated by reference herein.

FIELD OF THE INVENTION

The present invention generally relates to processes for preparing energy-dense biomass pellets for combustion, while also recovering fermentable sugars from the biomass.

BACKGROUND OF THE INVENTION

Wood and biomass burning is making a comeback after over century of domination by coal, petroleum, and natural gas for power generation. The availability of energy-dense fossil fuels and efficient transportation networks made centralized power production the technology of choice. In the 21st century, biomass heat and power plants and district heating are enjoying a renaissance. This popularity is driven in part by the carbon-neutral nature of most biomass (i.e., no net $CO_2$ emissions). The rising cost of fossil fuels and incentives for switching drive consumer decisions toward renewable energy. Also, renewable-energy portfolio mandates require that utilities construct renewable power plants.

One challenge to combusting biomass is its high moisture content. Living and freshly cut biomass typically contains moisture between 40% and 60%. In loose storage, the biomass dryness can reach air-dry moisture of about 10%. This drying of wood is slow, typically requiring at least a full summer season. This necessitates double handling and increases procurement cost. It can be advantageous to first pelletize biomass, which can drive moisture out of the biomass, by using part of the biomass energy, waste heat, or a fossil fuel. The final moisture from pelletizing is typically 5-7%, which is similar to moisture of coal. Boiler efficiencies increase approximately half a percent with each percentage removal of moisture.

In biomass, cellulose and hemicellulose each have about half of the calorific heat value of coal, because of high oxygen content of polymeric sugar constituents. Lignin has a similar calorific heat value to coal, but sulfur is nearly absent. The combined energy content of biomass is typically 8,000-9,000 Btu/lb, as compared to 10,000-14,000 Btu/lb in coal. Because of high oxygen content and moisture in biomass, the boiler efficiency for biomass firing typically ranges from 50-65%. A large portion of heat generated in combustion escapes as steam through the stack. Therefore, converting coal-burning boilers to biomass firing may reduce boiler capacity by as much as 60%. There is a need to maximize utilization of these assets, and therefore more energy-dense biomass is desired.

Feeding irregularly shaped biomass also represents a challenge. Pelletizing can produce uniformly sized material that does not bridge or lodge easily in a storage silo. On the other hand, the pelletized material can absorb moisture, if stored loosely outdoors.

Another obstacle is presented by the ash in the biomass. Ash content of biomass typically varies between 0.4% and 15%. Hardwood and softwood stem and forest trimmings contain only 0.4% to 0.8% ash that is rich in calcium and potassium. Other biomass materials including pulp and paper sludge, paper waste, recycled paper and construction waste, can contain up to 30% ash. Such ash includes minerals in plant capillaries, dirt on the surface, and coating in the paper. The wood exposed to salt water contains elevated levels of sodium and chlorides.

Agricultural residues of annual plants, such as corn stover, corn fiber, wheat straw, sugarcane bagasse, rice straw, oat straw, barley straw, and miscanthus can contain up to 10% or more ash that is rich in silica, potassium, and chlorine. The agricultural residue material is very lean in sulfur, typically less than 0.1%, versus coal sulfur content of 0.5-7.5%. Significant minerals in these annual agricultural residues include potassium, sodium, silica, calcium, and corrosive halogens such as chlorides.

Upon combustion at high temperatures, metals and halogens volatilize to aerosols and carry over from the boiler with flue gas. The cooling of fly ash creates microscopic particles that are found to cause respiratory illnesses. Flue-gas treatment for particulate removal includes cyclones, scrubbers, and electrostatic precipitators (ESP). These environmental controls in the central power plant are expensive and, in domestic applications, tend to be cost-prohibitive. Recent Maximum Achievable Control Technology (MACT) legislation by the U.S. EPA seeks to control particulate emissions from large biomass power plants. Other minerals such as calcium and silica remain in the bottom of the boiler and have tendency to form clinkers and to scale (slag) in the boiler tubes. Alkaline chloride salts can cause corrosion of the boiler tubes.

What are needed are processes and apparatus to prepare biomass, including wood and agricultural residues, into clean, energy-dense biomass for improved combustion, with or without pelletizing the biomass. The energy-dense biomass should be capable of being fired alone or in combination with another solid fuel. It would be desirable for these processes to also have good potential to recover various co-products, such as sugars, sugar fermentation products, furfural, levulinic acid, fertilizers, and lignin.

SUMMARY OF THE INVENTION

The present invention addresses the aforementioned needs in the art.

Some variations provide a process for producing biomass pellets and sugars from cellulosic biomass, the process comprising:

(a) providing a feedstock comprising cellulosic biomass;

(b) extracting the feedstock with steam and/or hot water under effective extraction conditions and optionally with an acid catalyst, to produce cellulose-rich solids and an extract liquor containing hemicellulosic oligomers and lignin;

(c) separating the cellulose-rich solids from the extract liquor;

(d) filtering the extract liquor to remove at least some of the lignin, thereby generating a filter permeate comprising cleaned extract liquor containing the hemicellulosic oligomers and a filter retentate comprising a lignin-rich stream;

(e) hydrolyzing the hemicellulosic oligomers in the cleaned extract liquor with an acid or enzymes, to generate hemicellulosic monomers;

(f) recovering the hemicellulosic monomers; and (g) pelletizing the cellulose-rich solids to form biomass pellets, wherein the pelletizing utilizes at least some of the lignin-rich stream from step (d) as a binder or binder component.

In some embodiments, step (b) includes use of the acid catalyst wherein the acid catalyst is an inorganic acid, an organic acid, or a combination thereof.

In some embodiments, step (d) utilizes membrane filtration with various membrane pore sizes possible. Optionally, step (d) comprises introducing a filter aid or an additive to enhance filtration of lignin.

In some embodiments, the binder or binder component further includes one or more high-molecular-weight compounds other than lignin. In these or other embodiments, the binder or binder component further includes acetic acid derived from the cellulosic biomass. In any of these embodiments, the binder or binder component may include sugar-degradation compounds derived from the cellulosic biomass, such as furfural, hydroxymethylfurfural, char, etc. In some embodiments, the binder or binder component further includes one or more external compounds not derived from the cellulosic biomass. Any external binder known in the art may be added to the lignin-based binder composition.

In some embodiments, the process further includes pressing, drying, grinding, torrefying, pyrolyzing, or otherwise treating the cellulose-rich solids before the pelletizing in step (g).

The biomass pellets may be combusted to produce energy, including heat and/or electricity. The biomass pellets may have an energy content from about 8,500 Btu/lb to about 12,000 Btu/lb on a dry basis, such as at least 9,000 Btu/lb or at least 10,000 Btu/lb on a dry basis.

In some embodiments, the process further comprises fermenting the hemicellulosic sugars to one or more fermentation products, such as but not limited to ethanol.

The order of steps may be varied in other embodiments. For example, step (e) may be carried out prior to step (d). In this manner, when hemicellulosic oligomers are hydrolyzed to monomers, lignin may be released from the oligomers and/or precipitate in the solution. It may be desired to carry out the hydrolysis and then filter out the lignin present in solution. Alternatively, filtration could be performed both before and after hydrolysis.

Other variations of the invention provide a process for producing biomass pellets from cellulosic biomass, the process comprising:

(a) providing a feedstock comprising cellulosic biomass;

(b) extracting the feedstock with steam and/or hot water under effective extraction conditions and optionally with an acid catalyst, to produce cellulose-rich solids and an extract liquor containing hemicellulosic oligomers and lignin;

(c) separating the cellulose-rich solids from the extract liquor;

(d) removing at least some of the lignin from the extract liquor, thereby generating cleaned extract liquor and a lignin-rich stream; and (e) pelletizing the cellulose-rich solids to form biomass pellets, wherein the pelletizing utilizes at least some of the lignin-rich stream from step (d) as a binder or binder component.

In some embodiments, step (d) utilizes filtration, such as membrane filtration. Other separation techniques may be utilized in step (d), including for example centrifugation, clarification, electrostatic precipitation, or reactive separation. Reactive separation may involve adjustment of one or more of temperature, pH, liquid composition, or residence time associated with a unit for the reactive separation.

In some embodiments, the process further comprises hydrolyzing the hemicellulosic oligomers in the cleaned extract liquor with an acid or enzymes, to generate hemicellulosic monomers, and then recovering the hemicellulosic monomers. Acids may include sulfuric acid, sulfurous acid, sulfur dioxide, lignosulfonic acids, nitric acid, nitrous acid, carbonic acid, acetic acid, formic acid, and so on. Enzymes, if employed, should have hemicellulose activity.

In some embodiments, the binder or binder component further includes one or more high-molecular-weight compounds other than lignin, such as sugar-degradation compounds (e.g., char) derived from the cellulosic biomass. Also, the binder may include components derived from biomass, but not from sugar degradation, such as acetic acid, uronic acids, or proteins. In certain embodiments, the binder or binder component further includes one or more external compounds not derived from the cellulosic biomass.

The present invention also provides biomass pellets (of any shape or size) and compositions thereof, as products produced by the disclosed process. The present invention also provides systems and apparatus to carry out the processes described.

BRIEF DESCRIPTION OF THE FIGURE

FIG. 1 is a simplified block-flow diagram depicting the process of some embodiments of the present invention. Dashed lines indicate optional streams.

DETAILED DESCRIPTION OF EMBODIMENTS OF THE INVENTION

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing reaction conditions, stoichiometries, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of"

limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of".

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for illustration purposes only.

Some variations provide a process for producing biomass pellets and sugars from cellulosic biomass, the process comprising:

(a) providing a feedstock comprising cellulosic biomass;

(b) extracting the feedstock with steam and/or hot water under effective extraction conditions and optionally with an acid catalyst, to produce cellulose-rich solids and an extract liquor containing hemicellulosic oligomers and lignin;

(c) separating the cellulose-rich solids from the extract liquor;

(d) filtering the extract liquor to remove at least some of the lignin, thereby generating a filter permeate comprising cleaned extract liquor containing the hemicellulosic oligomers and a filter retentate comprising a lignin-rich stream;

(e) hydrolyzing the hemicellulosic oligomers in the cleaned extract liquor with an acid or enzymes, to generate hemicellulosic monomers;

(f) recovering the hemicellulosic monomers; and (g) pelletizing the cellulose-rich solids to form biomass pellets, wherein the pelletizing utilizes at least some of the lignin-rich stream from step (d) as a binder or binder component.

In some embodiments, step (b) includes use of the acid catalyst wherein the acid catalyst is an inorganic acid, an organic acid, or a combination thereof In some embodiments, step (d) utilizes membrane filtration with various membrane pore sizes possible. Optionally, step (d) comprises introducing a filter aid or an additive to enhance filtration of lignin.

In some embodiments, wash filtrate is clarified from suspended material, such as fiber and sand by clarification or centrifugation. From the sedimentation, the clarified filtrate is then sent to an ultrafiltration step. The suspended solids are further concentrated in a filter press to form combustible product. At this point the clarified filtrate may be acidified to reduce microbial fouling of the membranes.

In some embodiments, ultrafiltration is used for lignin removal. The clarified filtrate leaving the sedimentation may be sent to a bank of ultrafiltration membrane elements. The ultrafiltration membrane may reject large dissolved molecules, such as lignin at molecular weights between 3,000 g/mol and 10,000 g/mol.

In some embodiments, the binder or binder component further includes one or more high-molecular-weight compounds other than lignin. In these or other embodiments, the binder or binder component further includes acetic acid derived from the cellulosic biomass. In any of these embodiments, the binder or binder component may include sugar-degradation compounds derived from the cellulosic biomass, such as furfural, hydroxymethylfurfural, char, etc. In some embodiments, the binder or binder component further includes one or more external compounds not derived from the cellulosic biomass. Any external binder known in the art may be added to the lignin-based binder composition.

In some embodiments, the process further includes pressing, drying, grinding, torrefying, pyrolyzing, or otherwise treating the cellulose-rich solids before the pelletizing in step (g).

The biomass pellets may be combusted to produce energy, including heat and/or electricity. The biomass pellets may have an energy content from about 8,500 Btu/lb to about 12,000 Btu/lb on a dry basis, such as at least 9,000 Btu/lb or at least 10,000 Btu/lb on a dry basis.

In some embodiments, the process further comprises fermenting the hemicellulosic sugars to one or more fermentation products, such as but not limited to ethanol.

The order of steps may be varied in other embodiments. For example, step (e) may be carried out prior to step (d). In this manner, when hemicellulosic oligomers are hydrolyzed to monomers, lignin may be released from the oligomers and/or precipitate in the solution. It may be desired to carry out the hydrolysis and then filter out the lignin present in solution. Alternatively, filtration could be performed both before and after hydrolysis.

Other variations of the invention provide a process for producing biomass pellets from cellulosic biomass, the process comprising:

(a) providing a feedstock comprising cellulosic biomass;

(b) extracting the feedstock with steam and/or hot water under effective extraction conditions and optionally with an acid catalyst, to produce cellulose-rich solids and an extract liquor containing hemicellulosic oligomers and lignin;

(c) separating the cellulose-rich solids from the extract liquor;

(d) removing at least some of the lignin from the extract liquor, thereby generating cleaned extract liquor and a lignin-rich stream; and (e) pelletizing the cellulose-rich solids to form biomass pellets, wherein the pelletizing utilizes at least some of the lignin-rich stream from step (d) as a binder or binder component.

In some embodiments, step (d) utilizes filtration, such as membrane filtration. Other separation techniques may be utilized in step (d), including for example centrifugation, clarification, electrostatic precipitation, or reactive separation. Reactive separation may involve adjustment of one or more of temperature, pH, liquid composition, or residence time associated with a unit for the reactive separation.

In some embodiments, the process further comprises hydrolyzing the hemicellulosic oligomers in the cleaned extract liquor with an acid or enzymes, to generate hemicellulosic monomers, and then recovering the hemicellulosic monomers. Acids may include sulfuric acid, sulfurous acid, sulfur dioxide, lignosulfonic acids, nitric acid, nitrous acid, carbonic acid, acetic acid, formic acid, and so on. Enzymes, if employed, should have hemicellulose activity.

Sulfuric acid or enzymes may be used to hydrolyze the sugar concentrate from the filter or membrane, into fermentable sugars. The reaction conditions for the acid hydrolysis may include, for example, 10 to 240 minutes of residence time at a temperature of 80 to 200° C. The pH of the solution during hydrolysis may be from about 0 to about 4. This low pH will convert polymeric hemicelluloses into monomer sugars. Time, temperature, and pH should be optimized to maximize sugar yield without converting monomer sugars further to furfural and other components which inhibit fermentation. Alternatively, enzymes such as a mixture of cellulase and xylanase enzymes can be used to perform hydrolysis.

In some embodiments, the binder or binder component further includes one or more high-molecular-weight compounds other than lignin, such as sugar-degradation compounds (e.g., char) derived from the cellulosic biomass. Also, the binder may include components derived from biomass, but not from sugar degradation, such as acetic acid, uronic acids, or proteins. In certain embodiments, the binder or binder component further includes one or more external compounds not derived from the cellulosic biomass.

"Biomass," for purposes of this disclosure, shall be construed as any biogenic feedstock or mixture of a biogenic and non-biogenic feedstock. Elementally, biomass includes at least carbon, hydrogen, and oxygen. The methods and apparatus of the invention can accommodate a wide range of feedstocks of various types, sizes, and moisture contents.

Biomass includes, for example, plant and plant-derived material, vegetation, agricultural waste, forestry waste, wood waste, paper waste, animal-derived waste, poultry-derived waste, and municipal solid waste. In various embodiments of the invention utilizing biomass, the biomass feedstock may include one or more materials selected from: softwood chips, hardwood chips, timber harvesting residues, tree branches, tree stumps, knots, leaves, bark, sawdust, off-spec paper pulp, cellulose, corn, corn stover, wheat straw, rice straw, sugarcane, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, carbohydrates, plastic, and cloth.

Selection of a particular feedstock or feedstocks is not regarded as technically critical, but is carried out in a manner that tends to favor an economical process. Typically, regardless of the feedstocks chosen, there can be (in some embodiments) screening to remove undesirable materials. The feedstock can optionally be dried prior to processing.

The feedstock employed may be provided or processed into a wide variety of particle sizes or shapes. For example, the feed material may be a fine powder, or a mixture of fine and coarse particles. The feed material may be in the form of large pieces of material, such as wood chips or other forms of wood (e.g., round, cylindrical, square, etc.). In some embodiments, the feed material comprises pellets or other agglomerated forms of particles that have been pressed together or otherwise bound.

The present invention also provides biomass pellets (of any shape or size) and compositions thereof, as products produced by the disclosed process. The present invention also provides systems and apparatus to carry out the processes described.

In some embodiments, the process starts as biomass is received or reduced to approximately ¼ thickness. In a first step of the process, the biomass chips are fed to a pressurized extraction vessel operating continuously or in batch mode. The chips may be steamed or water-washed to remove dirt and entrained air. The chips are immersed with aqueous liquor or saturated vapor and heated to a temperature between about 100° C. to about 250° C., for example 150° C., 160° C., 170° C., 180° C., 190° C., 200° C., or 210° C. Preferably, the chips are heated to about 180° C. to 210° C. The pressure in the pressurized vessel may be adjusted to maintain the aqueous liquor as a liquid, a vapor, or a combination thereof. Exemplary pressures are about 1 atm to about 30 atm, such as about 3 atm, 5 atm, 10 atm, or 15 atm.

The aqueous liquor may contain acidifying compounds, such as (but not limited to) sulfuric acid, sulfurous acid, sulfur dioxide, acetic acid, formic acid, or oxalic acid, or combinations thereof. The dilute acid concentration can range from 0.01% to 10% as necessary to improve solubility of particular minerals, such as potassium, sodium, or silica. Preferably, the acid concentration is selected from about 0.01% to 4%, such as 0.1%, 0.5%, 1%, 1.5%, 2%, 2.5%, 3%, or 3.5%.

A second step may include depressurization of the extracted chips. The vapor can be used for heating the incoming woodchips or cooking liquor, directly or indirectly. The volatilized organic acids (e.g., acetic acid), which are generated or included in the cooking step, may be recycled back to the cooking A third step may include washing the extracted chips. The washing may be accomplished with water, recycled condensates, recycled permeate, or combination thereof. A liquid biomass extract is produced. A countercurrent configuration may be used to maximize the biomass extract concentration. Washing typically removes most of the dissolved material, including hemicelluloses and minerals. The final consistency of the dewatered cellulose-rich solids may be increased to 30% or more, preferably to 50% or more, using a mechanical pressing device.

A fourth step may include drying of the extracted solids to a desired final moisture. The heat necessary for drying may be derived from combusting part of the starting biomass. Alternatively, or additionally, the heat for drying may be provided by other means, such as a natural gas boiler or other auxiliary fossil fuel, or from a waste heat source.

A fifth step may include preparing the biomass for pelletizing. This step may include refining, milling, fluidizing, compacting, torrefying, carbonizing, pressing, heating, cooling, and/or drying the extracted biomass. Using known equipment, biomass may be extruded through a pressurized chamber to form uniformly sized pellets (of any shape or size) or briquettes. Mild refining using a blow unit may be employed to disrupt the fibers and reduce particle size, since it may be beneficial to avoid longer fibers in pellets.

The energy-dense biomass pellets will generally have higher energy density compared to a process that does not extract hemicellulosic sugars from the feedstock prior to combustion.

In some embodiments, the extracted solids are fed to a torrefaction unit. Torrefaction is a form of mild pyrolysis at temperatures typically ranging between 200° C. to 325° C. During torrefaction, biomass properties are changed to obtain better fuel quality for combustion and gasification applications.

Torrefaction of biomass particles is well-known and is a process in which biomass particles are heated in a low-oxygen or oxygen-free environment. Volatile compounds within the particles are released, including water, and the cellular structure of the particles is degraded, resulting in a partial loss of mass and an increase in friability. Friability means the ability of a solid substance to be reduced to smaller pieces. Torrefaction also can enhance the moisture resistance of the solids. Torrefied particles have an enhanced energy value when measured in terms of heat energy per unit of weight. Torrefaction of biomass also can improve the grindability. This leads to more efficient co-firing in existing coal-fired power stations or entrained-flow gasification for the production of chemicals and transportation fuels.

The degree of torrefaction of biomass particles depends on several factors, including the level of heat applied, the length of time the heat is applied, and surrounding gas conditions (particularly with respect to oxygen level). Known biomass-torrefaction systems control the variables of heat, residence time, and oxygen levels to achieve consistent torrefied particles, typically employing mechanical means to convey the particles, such as rotating trays or screws.

In some embodiments, the energy density of the biomass pellet is from about 8,500 Btu/lb to about 12,000 Btu/lb on a dry basis, such as at least 9,000 Btu/lb or at least 10,000 Btu/lb on a dry basis.

A sixth step may be combustion of the biomass pellets. The biomass pellets are fed to a boiler and combusted, preferably with excess air, using well-known combustion apparatus. Boiler bottom may be fixed, moving, or fluidized for the best efficiency. The flue gas is cooled and fly ash is collected into gravity collectors.

The energy-dense biomass pellets have lower inorganic emissions potential compared to the original cellulosic biomass, in preferred embodiments. The reason is that the energy-dense biomass will contain lower ash content compared to a process that does not extract inorganic components from the feedstock prior to combustion, in the manner disclosed herein. In some embodiments, the extracted biomass is sufficiently low in ash such that when the extracted biomass is combusted, particulate matter emissions are very low. In certain embodiments, the particulate matter emissions are so low as to avoid the need for any additional cleaning device, and associated control system, in order to meet current emission regulations.

A seventh step may include treatment of the biomass extract to form a hydrolysate comprising fermentable hemicellulose sugars. In some embodiments, the biomass extract is hydrolyzed using dilute acidic conditions at temperatures between about 100° C. and 190° C., for example about 120° C., 130° C., 140° C., 150° C., 160° C., or 170° C., and preferably from 120° C. to 150° C.

The acid may be selected from sulfuric acid, sulfurous acid, or sulfur dioxide. Alternatively, or additionally, the acid may include formic acid, acetic acid, or oxalic acid from the cooking liquor or recycled from previous hydrolysis. Alternatively, hemicellulose enzymes may used instead of acid hydrolysis. The lignin from this step may be separated and recovered, or recycled to increase the binding and heating value of the pellets, or sent directly to the boiler.

An eighth step may include evaporation of hydrolysate to remove some or most of the volatile acids. The evaporation may include flashing or stripping to remove sulfur dioxide, if present, prior to removal of volatile acids. The evaporation step is preferably performed below the acetic acid dissociation pH of 4.8, and most preferably a pH selected from about 1 to about 2.5. The dissolved solids are concentrated, such as to about 10% to about 40% to optimize fermentable hemicellulose sugar concentration to a particular microorganism. *Saccharomyces Cerevisiae* fermentation can withstand dissolved solids concentrations of 30-50%, while *Clostridia Acetobutylicum* fermentation is viable at 10-20% concentrations only, for example.

In some embodiments, additional evaporation steps may be employed. These additional evaporation steps may be conducted at different conditions (e.g., temperature, pressure, and pH) relative to the first evaporation step.

In some embodiments, some or all of the organic acids evaporated may be recycled, as vapor or condensate, to the first step (cooking step) and/or third step (washing step) to remove assist in the removal of minerals from the biomass. This recycle of organic acids, such as acetic acid, may be optimized along with process conditions that may vary depending on the amount recycled, to improve the cooking and/or washing effectiveness.

Some embodiments of the invention enable processing of "agricultural residues," which for present purposes is meant to include lignocellulosic biomass associated with food crops, annual grasses, energy crops, or other annually renewable feedstocks. Exemplary agricultural residues include, but are not limited to, corn stover, corn fiber, wheat straw, sugarcane bagasse, rice straw, oat straw, barley straw, miscanthus, energy cane, or combinations thereof. In certain embodiments, the agricultural residue is sugarcane bagasse.

In some embodiments, the fermentable hemicellulose sugars are recovered from solution, in purified form. In some embodiments, the fermentable hemicellulose sugars are fermented to produce of biochemicals or biofuels such as (but by no means limited to) ethanol, 1-butanol, isobutanol, acetic acid, lactic acid, or any other fermentation products. A purified fermentation product may be produced by distilling the fermentation product, which will also generate a distillation bottoms stream containing residual solids. A bottoms evaporation stage may be used, to produce residual solids.

Following fermentation, residual solids (such as distillation bottoms) may be recovered, or burned in solid or slurry form, or recycled to be combined into the biomass pellets. Use of the fermentation residual solids may require further removal of minerals. Generally, any leftover solids may be used for burning as additional liquefied biomass, after concentration of the distillation bottoms.

Part or all of the residual solids may be co-combusted with the energy-dense biomass, if desired. Alternatively, or additionally, the process may include recovering the residual solids as a fermentation co-product in solid, liquid, or slurry form. The fermentation co-product may be used as a fertilizer or fertilizer component, since it will typically be rich in potassium, nitrogen, and/or phosphorous.

Optionally, the process may include co-combusting the recovered lignin with the energy-dense biomass, to produce power. The recovered lignin may be combined with the energy-dense biomass prior to combustion, or they may be co-fired as separate streams. When recovered lignin is combined with the energy-dense biomass for making pellets, the lignin can act as a pellet binder.

In certain embodiments, the process further comprises combining, at a pH of about 4.8 to 10 or higher, a portion of the vaporized acetic acid with an alkali oxide, alkali hydroxide, alkali carbonate, and/or alkali bicarbonate, wherein the alkali is selected from the group consisting of potassium, sodium, magnesium, calcium, and combinations thereof, to convert the portion of the vaporized acetic acid to an alkaline acetate. The alkaline acetate may be recovered. If desired, purified acetic acid may be generated from the alkaline acetate, such as through electrolytic reduction to acetic acid.

In some variations, Green Power+® technology, commonly assigned with the assignee of this patent application, may be employed or modified as taught in one or more patents or patent applications commonly assigned with this patent application and incorporated by reference herein. Some embodiments employ conditions described in U.S. Pat. No. 8,211,680, issued Jul. 3, 2012; and/or U.S. patent application Ser. Nos. 13/471,662; 13/026,273; 13/026,280; 13/500,917; 61/536,477; 61/612,451; 61/612,453; 61/624,880; 61/638,730; 61/641,435; 61/679,793; 61/696,360; or 61/709,960 including the prosecution histories thereof. Each of these commonly owned patent applications is hereby incorporated by reference herein in its entirety.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A process for producing biomass pellets and sugars from cellulosic biomass, said process comprising:
    (a) providing a feedstock comprising cellulosic biomass;
    (b) extracting said feedstock with steam and/or hot water under effective extraction conditions and optionally with an acid catalyst, to produce cellulose-rich solids and an extract liquor containing hemicellulosic oligomers and lignin;
    (c) separating said cellulose-rich solids from said extract liquor;
    (d) filtering said extract liquor to remove at least some of said lignin, thereby generating a filter permeate comprising cleaned extract liquor containing said hemicellulosic oligomers and a filter retentate comprising a lignin-rich stream;
    (e) hydrolyzing said hemicellulosic oligomers in said cleaned extract liquor with an acid or enzymes, to generate hemicellulosic monomers;
    (f) recovering said hemicellulosic monomers;
    (g) recovering acetic acid from said extract liquor and/or from said cleaned extract liquor; and
    (h) pelletizing said cellulose-rich solids to form biomass pellets, wherein said pelletizing utilizes at least some of said lignin-rich stream from step (d) as a binder or binder component, and wherein said pelletizing further utilizes at least some of said acetic acid from step (g) as a binder or binder component.

2. The process of claim 1, wherein step (b) includes use of said acid catalyst, wherein said acid catalyst is an inorganic acid, an organic acid, or a combination thereof.

3. The process of claim 1, wherein step (d) utilizes membrane filtration.

4. The process of claim 1, wherein step (d) comprises introducing a filter aid or an additive to enhance filtration of lignin.

5. The process of claim 1, wherein said binder or binder component further includes one or more high-molecular-weight compounds other than lignin.

6. The process of claim 1, wherein said binder or binder component further includes sugar-degradation compounds derived from said cellulosic biomass.

7. The process of claim 1, wherein said binder or binder component further includes one or more external compounds not derived from said cellulosic biomass.

8. The process of claim 1, said process further comprising torrefying said cellulose-rich solids before said pelletizing in step (h).

9. The process of claim 1, wherein said biomass pellets have an energy content from about 8,500 Btu/lb to about 12,000 Btu/lb on a dry basis.

10. A process for producing biomass pellets from cellulosic biomass, said process comprising:
    (a) providing a feedstock comprising cellulosic biomass;
    (b) extracting said feedstock with steam and/or hot water under effective extraction conditions and optionally with an acid catalyst, to produce cellulose-rich solids and an extract liquor containing hemicellulosic oligomers and lignin;
    (c) separating said cellulose-rich solids from said extract liquor;
    (d) removing at least some of said lignin from said extract liquor, thereby generating cleaned extract liquor and a lignin-rich stream;
    (e) recovering acetic acid from said extract liquor and/or from said cleaned extract liquor; and
    (f) pelletizing said cellulose-rich solids to form biomass pellets, wherein said pelletizing utilizes at least some of said lignin-rich stream from step (d) as a binder or binder component, and wherein said pelletizing further utilizes at least some of said acetic acid from step (e) as a binder or binder component.

11. The process of claim 10, wherein step (d) utilizes filtration, membrane separation, centrifugation, clarification, electrostatic precipitation, or a combination thereof.

12. The process of claim 11, wherein step (d) utilizes filtration.

13. The process of claim 10, said process further comprising hydrolyzing said hemicellulosic oligomers in said cleaned extract liquor with an acid or enzymes, to generate hemicellulosic monomers, and then recovering said hemicellulosic monomers.

14. The process of claim 10, wherein said binder or binder component further includes one or more high-molecular-weight compounds other than lignin.

15. The process of claim 10, wherein said binder or binder component further includes sugar-degradation compounds derived from said cellulosic biomass.

16. The process of claim 10, wherein said binder or binder component further includes one or more external compounds not derived from said cellulosic biomass.

17. The process of claim 10, said process further comprising torrefying said cellulose-rich solids before said pelletizing in step in (f).

18. The process of claim 10, wherein said biomass pellets have an energy content from about 8,500 Btu/lb to about 12,000 Btu/lb on a dry basis.

* * * * *